(12) United States Patent
Teige et al.

(10) Patent No.: US 7,726,815 B2
(45) Date of Patent: Jun. 1, 2010

(54) FOCUSING AND ASTIGMATISM COMPENSATION DEVICE FOR A FUNDUS CAMERA

(75) Inventors: Frank Teige, Jena (DE); Detlef Biernat, Jena (DE); Lothar Mueller, Ottendorf (DE)

(73) Assignee: Carl Zeiss Meditec AG, Jena (DE)

( * ) Notice: Subject to any disclaimer, the term of this patent is extended or adjusted under 35 U.S.C. 154(b) by 170 days.

(21) Appl. No.: 11/795,569

(22) PCT Filed: Feb. 7, 2006

(86) PCT No.: PCT/EP2006/001040

§ 371 (c)(1),
(2), (4) Date: Jul. 18, 2007

(87) PCT Pub. No.: WO2006/084654

PCT Pub. Date: Aug. 17, 2006

(65) Prior Publication Data

US 2008/0030682 A1    Feb. 7, 2008

(30) Foreign Application Priority Data

Feb. 9, 2005  (DE) ................. 10 2005 005 932

(51) Int. Cl.
A61B 3/14  (2006.01)

(52) U.S. Cl. .................... 351/206; 351/205

(58) Field of Classification Search .............. 351/206, 351/205, 200, 246, 221, 158, 41, 49
See application file for complete search history.

(56) References Cited

U.S. PATENT DOCUMENTS

| 4,795,248 | A | * | 1/1989 | Okada et al. ............... 351/158 |
| 5,255,026 | A | | 10/1993 | Arai et al. |
| 5,777,719 | A | | 7/1998 | Williams et al. |
| 5,815,233 | A | | 9/1998 | Morokawa et al. |
| 6,369,954 | B1 | | 4/2002 | Berge et al. |
| 7,216,981 | B2 | * | 5/2007 | Matsumoto ............... 351/205 |

FOREIGN PATENT DOCUMENTS

| DE | 40 03 211 C2 | 8/1990 |
| WO | WO 99/18456 | 4/1999 |
| WO | WO 03/000153 A2 | 1/2003 |
| WO | WO 2004/049927 A1 | 6/2004 |
| WO | WO 2005/060823 A1 | 7/2005 |

\* cited by examiner

Primary Examiner—Hung X Dang
(74) Attorney, Agent, or Firm—Patterson, Thuente, Christensen, Pedersen, P.A.

(57) ABSTRACT

The invention relates to a device for observing the ocular fundus, in particular to a fundus camera. Said device comprises a light source (1b) for the provision of illumination radiation, an illumination optical path for directing the illumination radiation onto the ocular fundus and observation optics for reproducing the illuminated ocular fundus, the observation optics comprising a module (16b), whose refractive power can be electrically adjusted.

17 Claims, 7 Drawing Sheets

FOCUSING AND ASTIGMATISM COMPENSATION DEVICE FOR A FUNDUS CAMERA

FIELD OF THE INVENTION

The invention relates to a device for examining the ocular fundus by means of an optical system and in particular by means of electronic sensors for recording images, preferably a fundus camera. The invention furthermore relates to an astigmatism compensation device, in particular for a fundus camera.

BACKGROUND OF THE INVENTION

Normally when using a fundus camera, depending on the defective vision of the patient, the optical observation system in the fundus camera is changed from one patient to the next such that a highly focused image of the ocular fundus is reproduced on the image recording sensor. In order to be able to examine as many patients as possible the focusing range is selected with no less than ±25 dpt. In known fundus cameras, either a part of the optical system is displaced along the optical axis of the lens, or the image recorder is displaced along the optical axis (see FIGS. 1a, 1b).

It has been demonstrated that the known fundus cameras require precise mechanical components that are expensive in and of themselves and in addition are subject to wear, and that furthermore it is not possible to obtain focused images of the ocular fundus in all patients using this camera.

However, the object of the invention is to provide a device for observing the ocular fundus that makes it possible, in a simpler manner and/or for a greater majority of patients, to obtain focused images of their ocular fundus.

SUMMARY OF THE INVENTION

This object is attained using the device for observing an ocular fundus in accordance with claim 1, using the astigmatism compensation device in accordance with claim 7, and using the adjustable lens in accordance with claim 10.

One aspect of the invention provides a device for observing an ocular fundus that has observation optics with a lens that is electrically adjustable with respect to its refractive power. The refractive power that can be adjusted in this manner can be a spherical or/and cylindrical refractive power; in the latter case, the axis position for the cylindrical refractive power can also be adjustable. The device can include in particular an electronic image recording sensor and/or can be embodied for direct visual observation. The electrically adjustable lens can have liquid crystal layers or two fluids contained in a container, between which fluids a phase boundary surface is embodied that can be deformed by applying a voltage.

A second aspect of the invention provides an astigmatism compensation device that includes a lens with adjustable radially asymmetric refractive power, the lens including two electrodes between which an electrical field is embodied when a voltage is applied.

A third aspect of the invention provides an adjustable lens, the lens including two fluids contained in a container, between which fluids is embodied a phase boundary surface that can be radially asymmetrically deformed by applying a voltage.

Additional advantageous details and aspects proceed from the subordinate claims, the following description, and the drawings.

BRIEF DESCRIPTION OF THE DRAWINGS

FIG. 5a

DETAILED DESCRIPTION

Figure 1A:
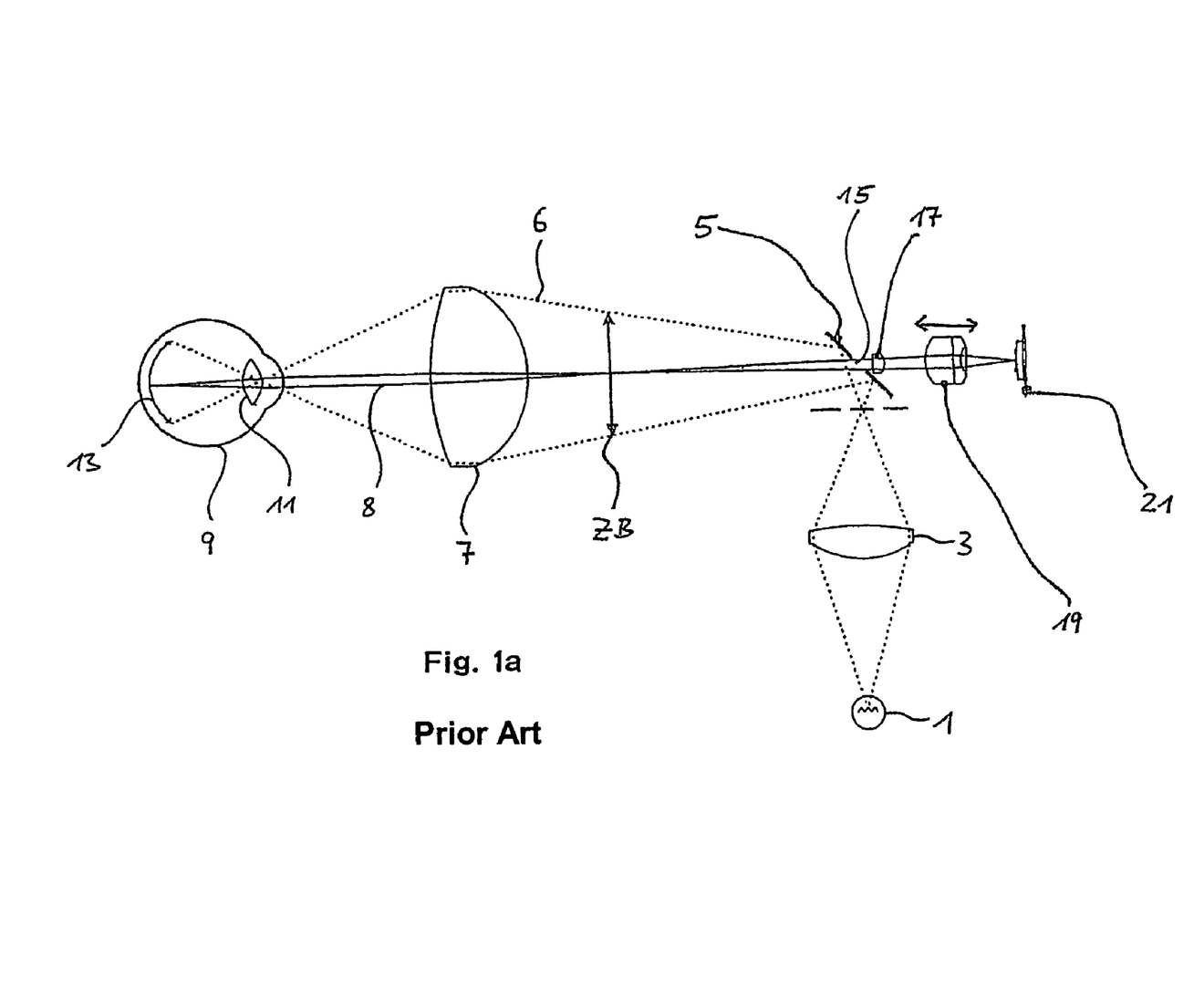
FIG. 1a depicts a conventional fundus camera with an optical system to be displaced.

In the known camera in accordance with FIG. 1a, light from a light source 1 is directed through a lens 3 onto a perforated mirror 5. From the perforated mirror 5, the illuminating light 6 is directed through a front lens 7 of the fundus camera onto the eye 9, and thus through the eye lens 11, onto the fundus 13 of the eye. The beam going out from the fundus 13 of the eye is directed through the eye lens 11 and the front lens 7 of the fundus camera onto the aperture 15 in the aperture mirror 5. A compensation lens 17 can be pivoted behind the aperture 15. Finally, the observation beam 8 is reproduced on an image recording sensor 21 through a main lens group 19 that is displaceable in the direction of the beam path.

Figure 1B:
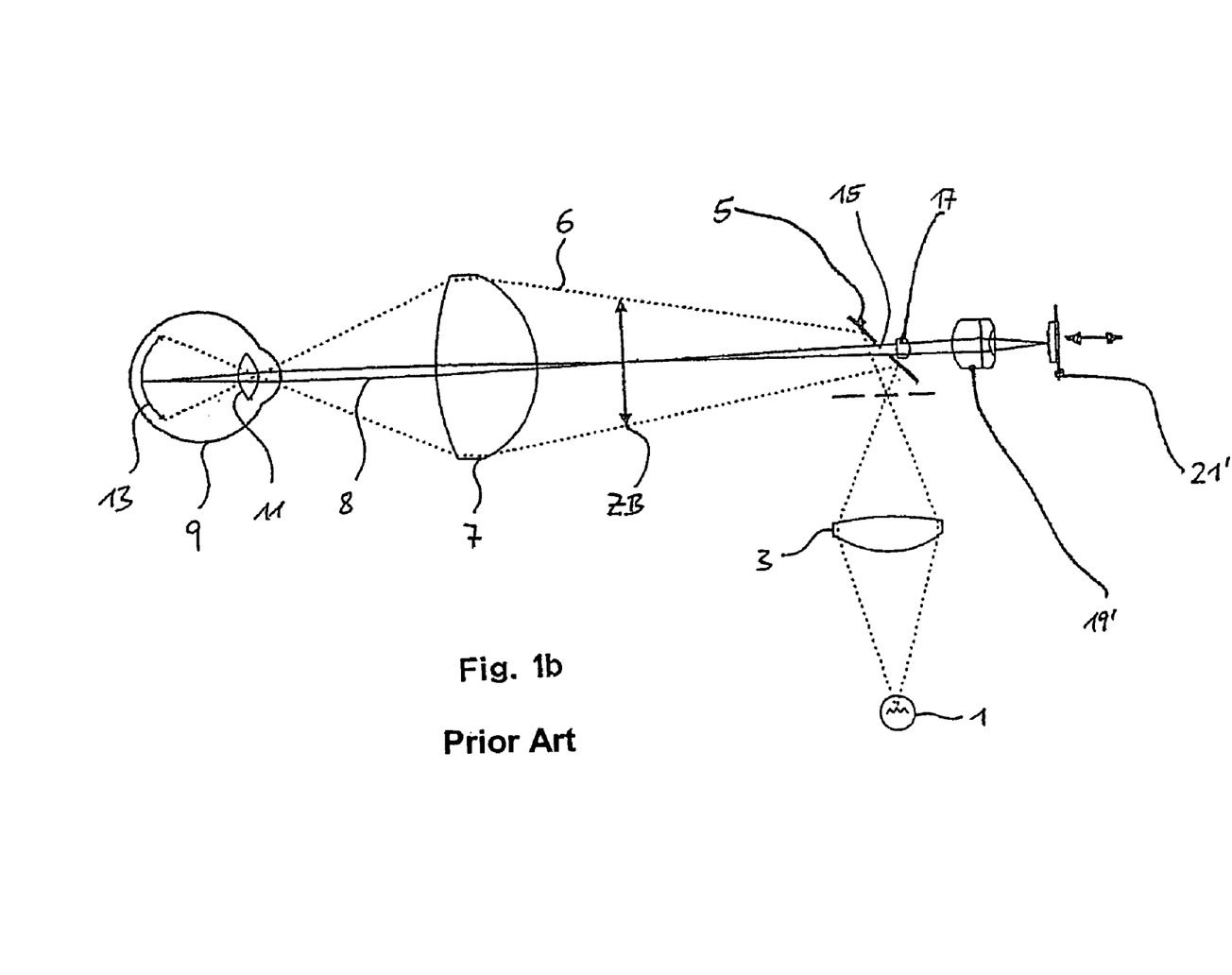
FIG. 1b depicts another conventional fundus camera with image recorder to be displaced.

In the known variant, in accordance with FIG. 1b, the components are basically arranged in the same manner, but the image recording sensor 21', rather than the main lens group 19', is displaceable in the direction of the beam path. In both variants, ZB is an intermediate image plane.

Figure 2:
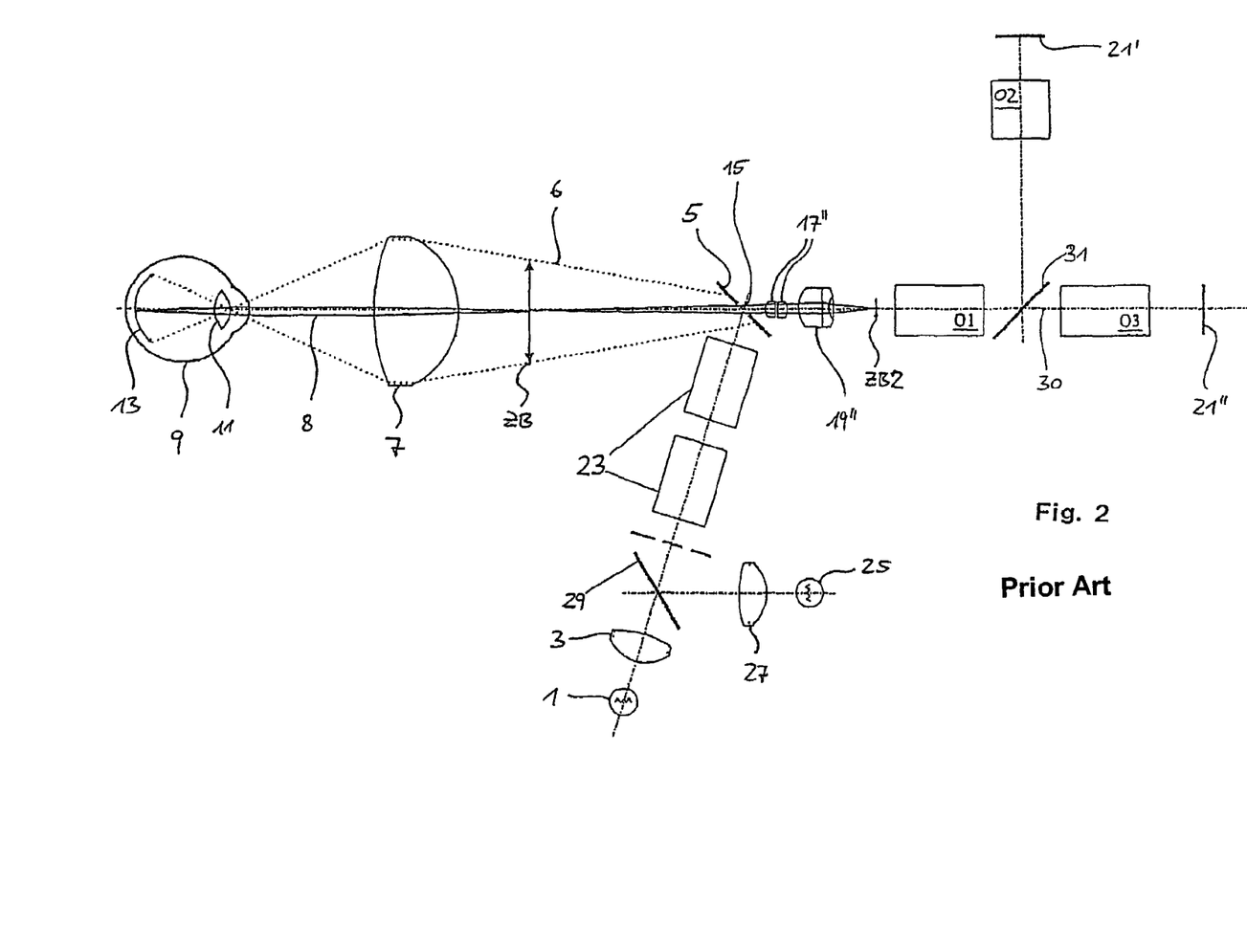
FIG. 2 depicts another conventional fundus camera with a Stokes lens as astigmatism compensation device.

In another known variant, in accordance with FIG. 2, the compensation lens is embodied as a Stokes lens pair 17" with which an astigmatism of the eye 9 can be compensated according to rate and direction by mechanically adjusting the axis position of the two lenses. In this case, the main lens group 19" produces a second intermediate image ZB2, which using multi-part imaging optics O1 is first reproduced on a folding mirror 31 and then either through rangefinder optics O2 on the CCD sensor of a rangefinder camera 21' or through documentation optics O3 on the CCD sensor of a documentation camera 21". In addition, a flash light 25 with associated optics 27 is provided in the illuminating beam path, and its light can be directed via an illuminating folding mirror 29 and additional illuminating optics 23 onto the aperture mirror 5.

Figure 3:
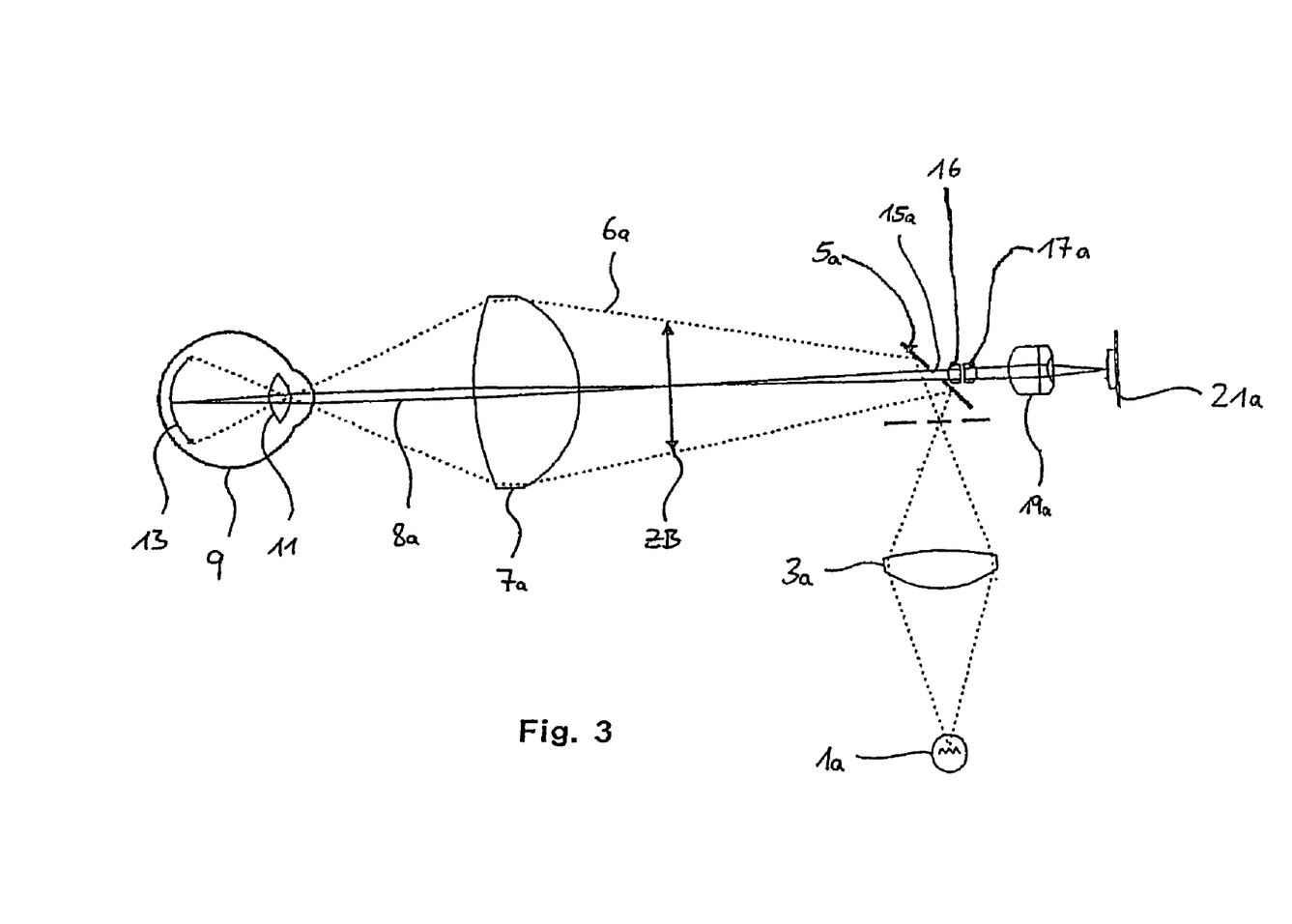
FIG. 3 depicts an inventive fundus camera with an electrically controllable lens.

Compared to the known fundus camera in accordance with FIG. 1a or 1b, the first embodiment depicted in FIG. 3 and the main lens group 19a as well as the image recording sensor 21a are securely mounted. Depending on their structure or function, components comparable to the components described in the foregoing will now and hereafter be labeled with the same numbers, but for purposes of differentiation these will be followed by lower-case letters. In this example, a pivotable compensating lens 17a for roughly adapting to the refractive power of the patient eye is also provided, but it can be omitted. In this example, an electrically adjustable lens 16 is arranged between aperture 15a and compensating lens 17a. The position between aperture 15a and main lens group 19a is preferred for the arrangement of the adjustable lens 16 because at this location the observation beam 8a has a relatively small diameter and therefore it is possible for the adjustable lens 16 to have a smaller free diameter. However, instead of the aperture mirror 5a, another beam splitter can be used to inject the illuminating light into the observation beam path, for instance a geometric beam splitter such as for instance a simple mirror, without an aperture, arranged in a lateral half of the beam.

Figure 4:
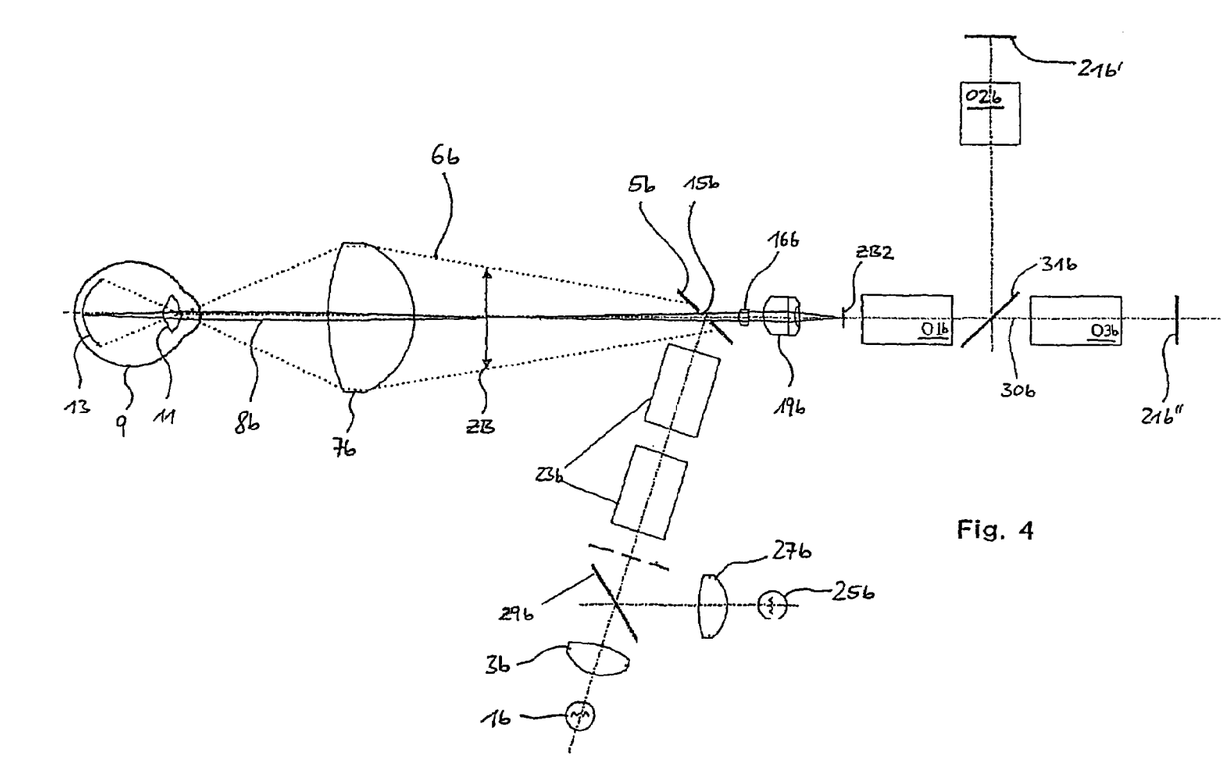
FIG. 4 depicts another inventive fundus camera with an electrically controllable astigmatism compensation device.

In the second embodiment, illustrated in FIG. 4, in contrast to the known variant in accordance with FIG. 2, an electrically adjustable lens 16b is arranged between the aperture 15b of the aperture mirror 5b and the main lens group 19b instead of the Stokes lens pair. This electrically adjustable lens 16b is embodied such that it has two adjustable refractive powers that can be adjusted independent of one another and the main directions of which are perpendicular to one another. For instance, the refractive power adjustment can be based on liquid crystal layers such as are described in U.S. Pat. Nos. 4,795,248 and 5,815,233. Full disclosure of these publications is included in the present application by reference.

Figure 5A:
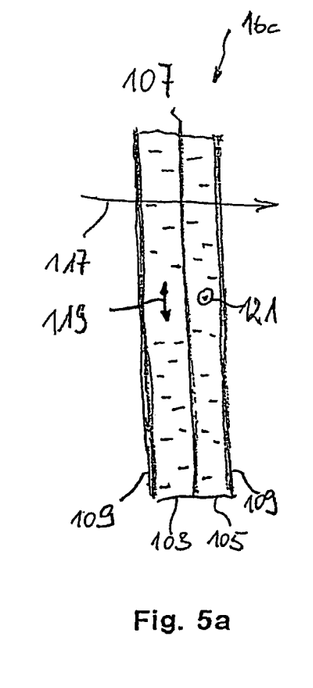
Figure 5B:
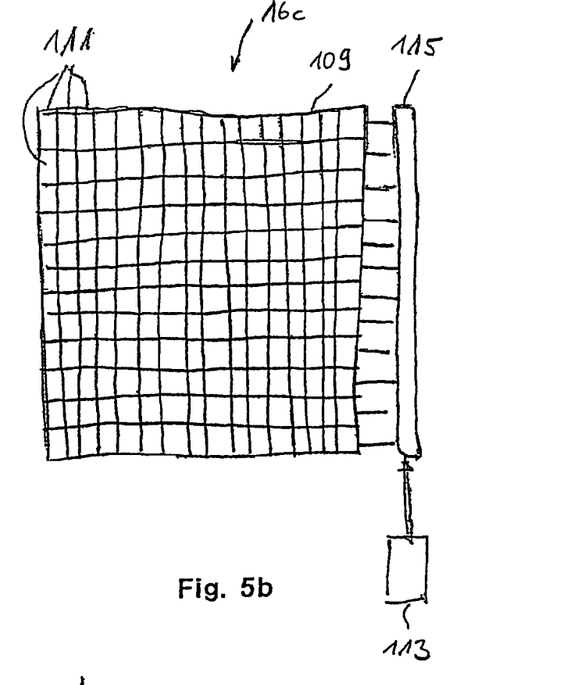
FIG. 5b depict a cross-section and elevation of an electro-optical lens with a liquid crystal basis.

FIG. 5a is a cross-section of an assembly 16c that has variable optical effect. The assembly 16c includes a first liquid crystal layer 103 and a second liquid crystal layer 105 that are arranged on either side of a common transparent continuous electrode 107. A likewise transparent electrode structure 109 is provided on a side of the common electrode 107 that opposes the liquid crystal layer 103, as is depicted in FIG. 5b. The electrode structure 109 provides a plurality of controllable pixels 111 that are arranged, for instance, in a rectangular grid. A control 113 is provided in order to apply an adjustable voltage to each pixel 111 via a driver 115 that feeds the voltage to the individual pixels as is already known for liquid crystal displays. Because of this, an electrical field is adjustable between each pixel 111 and the common electrode 107, and depending on the adjusted electrical field the liquid crystal layer 103 provides for a beam of light

117 passing there through a variable optical path length for a polarization direction of the beam 117. Arranged on a side of the liquid crystal layer 105 that faces away from the common electrode 107 is another transparent electrode structure 109 having the structure depicted in FIG. 5b that is likewise controlled by the control 113. While the liquid crystal layer 103 provides the variable optical path length for a polarization direction indicated by an arrow 119 in FIG. 5a in the plane of the figure, the liquid crystal layer 105 provides a correspondingly variable optical path length for a polarization direction orthogonal thereto, as is indicated by the symbol 121 in FIG. 5a.

Thus, using appropriate control of the electrode structure 109, it is possible to provide for both polarization directions of the beam 117 optical path lengths of the two liquid crystal layers 103, 105 that are adjustable as a function of a position on the layers 103, 105. Thus the assembly 16c can be controlled overall in order to provide adjustable optical effects for the beam 117, such as for instance, a round lens effect with positive or negative refractive power in terms of a selectable optical axis, or even a cylinder lens effect with positive or negative refractive power in terms of an adjustable plane of symmetry.

Figure 6:
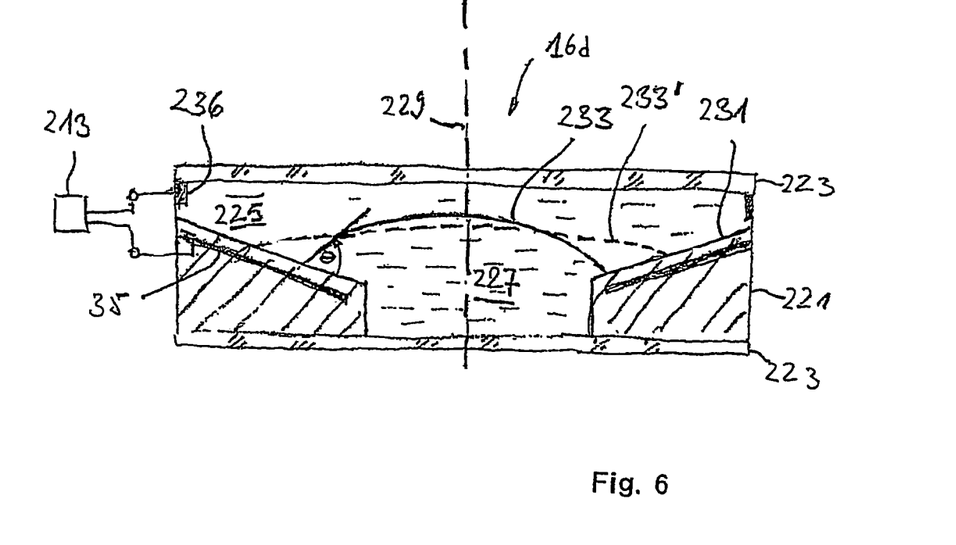
FIG. 6 depicts a cross-section of an electro-optical lens with a fluid basis.
Figure 7:
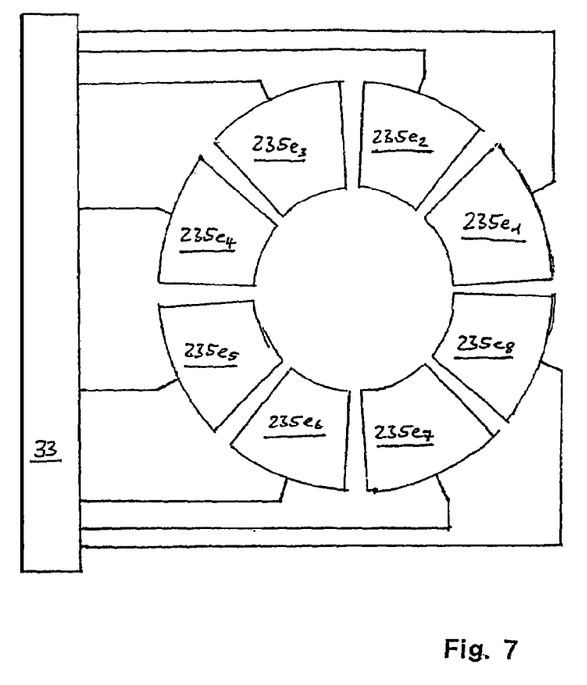
FIG. 7 is a diagram of an electrode arrangement for the lens depicted schematically in FIG. 6.

On the other hand, the refractive power setting can be based on lenses with two fluids separated by a phase boundary surface, as is sold by the Varioptic Company, 69007 Lyon, France. The way such lenses function is described, for instance, in international patent application WO 1999/018456; full disclosure of this publication is included in the present application by reference. FIG. 6 illustrates a section through such an optical assembly 16d that has an adjustable optical effect. The assembly 16d includes a housing 221 with two inlet and outlet windows 223, between which are enclosed two non-miscible liquids 225 and 227 that have different refractive indices. The one liquid 225 is, for instance, water or salt water and the other liquid 227 is, for instance, oil or a methylphenyl siloxane mixture with a density that is preferably the same as or similar to that of the water or salt water. The housing 221 provides for the two liquids 225, 227 a conical wall 231 that is symmetrical with respect to an optical axis 229 of the assembly and against which a boundary surface 233 is positioned between the two liquids at a contact angle θ. A likewise conical electrode 235 is arranged inside the wall 231, and an annular electrode 236 is arranged in the volume of the liquid 225 in the vicinity of the window 223. The liquid 225 is electrically conducting, while the liquid 227 is largely not electrically conducting. A voltage can be adjusted between the electrodes 235 and 236 using a control 213. A change in the voltage between the electrodes 235 and 236 alters the angle θ, which the boundary surface 233 creates between the two liquids 225, 227 with the wall 231. Thus, by changing the voltage between the electrodes 235, 236, it is possible to change the shape and curvature of the boundary surface 233, as is schematically depicted with a broken line 233' in FIG. 6. Due to the different refractive indices of the two liquids 225, 227, a lens effect of the assembly 16d can be changed for a light beam passing therethrough along the optical axis 229. If the conical electrode 235 is divided into a plurality of separately controllable sectors $235e_1$ through $235e_8$, as is depicted schematically in FIG. 7, another contact angle can be embodied in each sector $235e_1$ through $235e_8$. For providing a cylindrical or toroidal boundary surface with different refractive indices in main planes of curvature that are perpendicular to one another, diametrically opposing sectors are activated by a control 33 with an equal, maximum voltage (for instance, sectors $235e_1$ and $235e_5$), and the sectors arranged perpendicular thereto (for instance, sectors $235e_3$ through $235e_7$) with a minimum voltage that is the same for each of them (for instance, 0 V). Sectors located therebetween (for instance, sectors $235e_2$, $235e_4$, $235e_6$, and $235e_8$) are actuated by the control 33 with voltages therebetween. The more sectors provided, the finer the voltage graduation can be and the more exact the toroidal boundary surface that can be produced. However, it is preferred to provide at least 4 and up to 64 sectors; furthermore it is preferred to provide an even number of sectors, in particular a number of sectors that is divisible by four. The lens arrangement 16d can also be mounted such that it is rotatable in order to facilitate coarse adjustment onto the axis position of an astigmatism of a patient's eye; in this case the control 33 would only provide the fine adjustment for the voltage.

Figure 8:
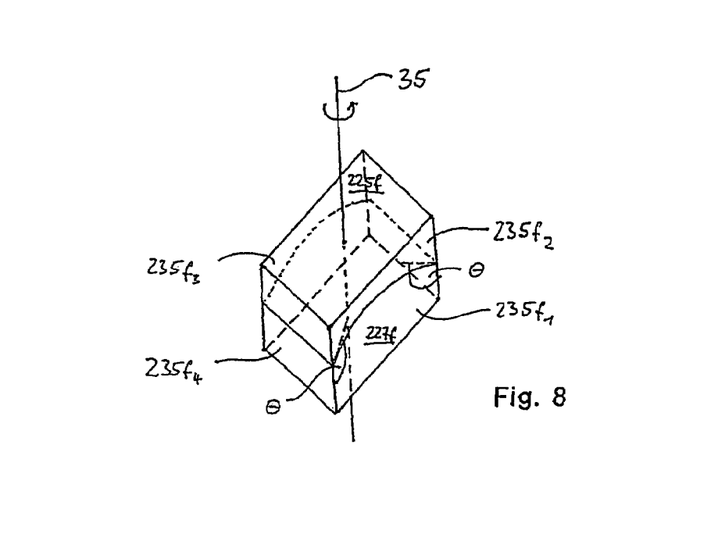
FIG. 8 is another electro-optical lens with a fluid basis.

However, it is also possible to provide a cuboid geometry 16f instead of the radially symmetrical geometry for the assembly 16d, and to arrange a flat electrode $235f$ through $235f_4$ in each of the four vertically stacked circumferential walls instead of a sectored, conically shaped electrode (see FIG. 8). The electrodes are each insulated from the adjacent electrode, but can be connected in an electrically conducting manner to the respective opposing electrode. For creating a cylindrical boundary surface between the fluids $225f$ and $227f$, a contact angle of 90° is set on two mutually opposing walls (for instance, electrodes $235f_1$ and $235f_3$), while another contact angle θ is set on the two other walls (for instance electrodes $235f_2$ and $235f_4$). This results in a cylindrically shaped boundary surface that can compensate an eye astigmatism in a patient according to the rate. In order to be able to adjust this arrangement onto the axis position of the eye astigmatism of the patent, it is preferably rotatably borne about its optical axis 35.

Compared to known devices for compensating cylindrical defects of the eye, the inventive device is clearly more simple to manufacture and to use. The optical components are simpler and do not require any rotary movement or require only a rotary movement that is simple to produce. In particular the optical components and the image recorder do not have to be displaceable, that is, they can be fixed and are therefore easier to adjust.

For instance, in the known device in accordance with FIG. 2, the rate of the cylindrical refractive power provided by the Stokes lens 17" for astigmatism compensation is determined by the angle of the relative arrangement of the Stokes lenses 17"; this relative angle must therefore be precisely adjusted. Consequently, the axis positions of both lenses in the Stokes lens pair 17" must be able to be precisely adjusted independent of one another. In contrast, in the present invention only the axis position of the overall arrangement must be adjusted, relative to the patient's eye, by rotating the device, for which lower precision is sufficient. The rate of the cylindrical refractive power for compensating astigmatism, however, can be adjusted electrically using the amount of voltage applied and therefore does not require such a precise mechanism.

Moreover, in contrast to the known devices, the actually adjusted cylinder value, including rate, [mathematical] sign, and axis position in the form of the control voltages, for the electrically activated lens and via the position of the activated electrodes or the adjusted angle of the adjustable lens assembly is easily evaluated and simply accessible for a follow-on documentation or computing process (for instance measurements, focusing, automatic focusing, etc.). The control can provide an output signal for this as well.

In addition, with the inventive device it is possible, using a differently measured refractive power of the patient's eye, to automatically adjust the compensation lens of the fundus camera electrically such that an optimally focused image of the ocular fundus can be recorded and/or observed. For this, the control can also have an input interface and/or a keyboard. In the latter case, data representing the refractive power of the patient's eye can be stored for instance in an electronically stored table together with identifying information for the patient; inputting the patient identification and an activation command can then initiate camera focusing. This makes it much easier to perform a series of examinations on a number of patients one after the other, even if the examinations of both eyes of the same patient normally require different settings for the compensation optics.

The invention can be employed not only for adult human patients, but also, due to its temporal advantages because the camera can be focused more rapidly, is particularly advantageous for children and vertebrate animals in general, especially mammals, in particular house pets such as dogs and cats, because the behavior of both children and animals (pets) during lengthy examinations can be problematic.

The invention claimed is:

1. A fundus camera device for observing an ocular fundus, comprising:
   a light source to provide illumination radiation,
   optics defining an illumination radiation path for directing the illumination radiation onto the ocular fundus, and
   observation optics for imaging the illuminated ocular fundus,
   the observation optics including an adjustable assembly whose refractive power is electrically adjustable in spherical, cylindrical or spherocylindrical refractive power.

2. The device in accordance with claim 1, wherein the adjustable assembly is electrically adjustable in axis position for the cylindrical refractive power.

3. The device in accordance claim 1, further including an electronic sensor to record an image of an ocular fundus that is imaged thereon.

4. A fundus camera device for observing an ocular fundus, comprising:
   a light source to provide illumination radiation,
   optics defining an illumination radiation path for directing the illumination radiation onto the ocular fundus, and
   observation optics for imaging the illuminated ocular fundus,
   the observation optics including an adjustable assembly whose refractive power is electrically adjustable wherein the electrically adjustable assembly comprises a container and two fluids contained in the container, the two fluids meeting at a phase interface boundary, and at least two electrodes between which, when a voltage is applied, an electrical field is produced that passes through at least one of the two fluids and deforms the boundary.

5. A fundus camera device for observing an ocular fundus, comprising:
   a light source to provide illumination radiation,
   optics defining an illumination radiation path for directing the illumination radiation onto the ocular fundus, and
   observation optics for imaging the illuminated ocular fundus,
   the observation optics including an adjustable assembly whose refractive power is electrically adjustable wherein the electrically adjustable assembly comprises an astigmatism compensation device with an optical axis, to compensate for astigmatism of an eye arranged on the optical axis, comprising: an optical assembly that is arranged on the optical axis, the optical assembly including at least two electrodes arranged such that, when a voltage is applied across the at least two electrodes, the assembly provides a radially asymmetric refractive power along the optical axis.

6. The device in accordance with claim 5, wherein the optical assembly is adjustable in axis position for cylindrical refractive power.

7. A fundus camera device for observing an ocular fundus, comprising:
   a light source to provide illumination radiation,
   optics defining an illumination radiation path for directing the illumination radiation onto the ocular fundus, and
   observation optics for imaging the illuminated ocular fundus,
   the observation optics including an adjustable assembly whose refractive power is electrically adjustable wherein the electrically adjustable assembly comprises:
   an adjustable lens, including:
   a container;
   a first fluid contained in the container;
   a second fluid that is contained in the container and that forms an interface boundary with the first fluid;
   a first electrode;
   at least one second electrode that is arranged relative to the first electrode such that, when a voltage is applied across the electrodes, an electrical field that passes through at least one of the fluids is produced such that the boundary interface assumes a rotationally asymmetrical shape.

8. The device in accordance with claim 7, wherein, when voltage is applied, the boundary interface assumes a substantially toroidal shape.

9. The device in accordance with claim 7, wherein, when voltage is applied, the boundary interface assumes a substantially cylindrical shape.

10. An astigmatism compensation device with an optical axis, to compensate for astigmatism of an eye arranged on the optical axis, comprising: an optical assembly that is arranged on the optical axis and that has electrically adjustable refractive power, the optical assembly including at least two electrodes arranged such that, when a voltage is applied across the at least two electrodes, the assembly provides a radially asymmetric refractive power along the optical axis.

11. The astigmatism compensation device in accordance with claim 10, wherein the optical assembly is adjustable in axis position for cylindrical refractive power.

12. The astigmatism compensation device in accordance with claim 10, wherein the optical assembly comprises: an adjustable lens, including:
    a container;
    a first fluid contained in the container;
    a second fluid that is contained in the container and that forms an interface boundary with the first fluid;
    a first electrode; and
    at least one second electrode that is arranged relative to the first electrode such that, when a voltage is applied across the electrodes, an electrical field that passes through at least one of the fluids is produced such that the boundary interface assumes a rotationally asymmetrical shape.

13. The astigmatism compensation device in accordance with claim 12, wherein, when voltage is applied, the boundary interface assumes a substantially toroidal shape.

14. The astigmatism compensation device in accordance with claim 12, wherein, when voltage is applied, the boundary interface assumes a substantially cylindrical shape.

15. An adjustable lens, comprising:
    a container;
    a first fluid contained in the container;
    a second fluid that is contained in the container and that forms an interface boundary with the first fluid;
    a first electrode;
    at least one second electrode that is arranged relative to the first electrode such that, when a voltage is applied across the electrodes, an electrical field that passes through at least one of the fluids is produced such that the boundary interface assumes a rotationally asymmetrical shape.

16. The adjustable lens in accordance with claim 15, wherein, when voltage is applied, the boundary interface assumes a substantially toroidal shape.

17. The adjustable lens in accordance with claim 15, wherein, when voltage is applied, the boundary interface assumes substantially cylindrical shape.

* * * * *